United States Patent [19]

Hart

[11] 4,396,383

[45] Aug. 2, 1983

[54] MULTIPLE CHAMBER SOLUTION CONTAINER INCLUDING POSITIVE TEST FOR HOMOGENOUS MIXTURE

[75] Inventor: John W. Hart, Winnetka, Ill.

[73] Assignee: Baxter Travenol Laboratories, Inc., Deerfield, Ill.

[21] Appl. No.: 319,491

[22] Filed: Nov. 9, 1981

[51] Int. Cl.³ ........................ A61J 1/00; B65D 30/22; A61M 5/00

[52] U.S. Cl. ........................................ 604/56; 604/82; 604/87; 604/404; 604/410; 604/416

[58] Field of Search ...................... 604/56, 81, 82, 87, 604/89, 91, 404, 408, 410, 416, 262; 150/2.5, DIG. 1; 215/1 C, 6, DIG. 3, DIG. 8

[56] References Cited

U.S. PATENT DOCUMENTS

| | | | |
|---|---|---|---|
| 2,714,974 | 8/1955 | Sawyer . | |
| 3,064,802 | 11/1962 | Jess et al. . | |
| 3,110,308 | 11/1963 | Bellamy, Jr. . | |
| 3,685,795 | 8/1972 | Caster . | |
| 3,762,399 | 10/1973 | Riedell | 604/408 |
| 3,911,918 | 10/1975 | Turner | 604/410 |
| 3,985,135 | 10/1976 | Carpenter et al. | 604/410 |
| 4,140,162 | 2/1979 | Gajewski et al. . | |
| 4,191,231 | 3/1980 | Winchell et al. . | |
| 4,195,632 | 4/1980 | Parker et al. . | |
| 4,198,972 | 4/1980 | Herb | 604/408 |
| 4,258,723 | 3/1981 | McCue et al. | 604/56 |
| 4,259,952 | 4/1981 | Avoy | 604/82 |
| 4,267,837 | 5/1981 | Purdy et al. | 604/82 |
| 4,294,247 | 10/1981 | Carter et al. . | |
| 4,336,802 | 6/1982 | Stone et al. | 604/416 |
| 4,340,049 | 7/1982 | Munsch . | |

OTHER PUBLICATIONS

Nutriflex[R] Container by Vifor, S. A. of Geneva, Switzerland; additional identification marks are "Twin--Flex, " No. 560, and 32/750.

*Primary Examiner*—Richard J. Apley
*Assistant Examiner*—Michelle N. Lester
*Attorney, Agent, or Firm*—Paul C. Flattery; John P. Kirby, Jr.; Bradford R. L. Price

[57] ABSTRACT

A container having a unique two chamber construction provides for the passive mixing of two supply solutions having different specific gravities into a single homogenous solution in a closed environment. The container includes means for a positive test that a single homogenous solution has been achieved. The container is especially useful for storing and mixing two supply solutions which when mixed form a single medical solution which itself is unsuitable for storage over extended time periods.

8 Claims, 11 Drawing Figures

MULTIPLE CHAMBER SOLUTION CONTAINER INCLUDING POSITIVE TEST FOR HOMOGENOUS MIXTURE

DESCRIPTION

1. Technical Field

The present invention relates to multiple chamber solution containers, and in particular to a flexible container for the storage and passive mixing of two medical fluids having different specific gravities.

2. Background of the Invention

There exist medical fluids which, because they are made by combining ingredients, are not stable over time. The medical fluids may suffer from product degradation or reduced efficacy during storage. A reasonable storage period is however necessary to permit production of the medical fluid, transportation to the hospital and storage within the hospital.

As an example, amino acid and dextrose are combined to form a parenteral solution for intravenous administration to a patient. If amino acid and dextrose are combined in a single container and then stored for many weeks or months, discoloration takes place.

Because of this basic incompatibility over time, amino acids and dextrose are sold separately. If a doctor prescribes a combined amino acid and dextrose solution for a patient, a hospital pharmacy must combine the amino acid solution and dextrose solution from two separate containers. The transfer of fluid from one container to another is time consuming and requires additional means such as transfer tubing and connectors between the two separate containers.

The procedure also provides an additional opportunity for fluid contamination. An amino acid/dextrose solution is an excellent growth medium for bacteria and therefore extreme care must be taken in the hospital pharmacy to ensure that the transfer occurs under virtually sterile conditions.

in order to remove the risk of contamination there are known containers having more than one chamber. The chambers are segregated but selective communication is possible through the use of a breakaway valve between the chambers which may be opened from outside the container by bending the container walls.

An improved multiple chamber container is described in U.S. patent application Ser. No. 246,479, Frank M. Richmond, Kenneth W. Larson and Robert A. Miller, inventors, filed on Mar. 23, 1981 and assigned to the present assignee. As shown in that application, a flexible, plastic container is separated into two chambers by means of a heat seal. A breakaway valve is mounted in a piece of tubing through the chamber-defining heat seal. When the valve is broken, the two chambers are in fluid communication through the piece of tubing. The tube prevents the opened valve from floating freely within one of the chambers. In addition, slots or openings may be made in the tube to facilitate fluid flow upon opening of the valve.

A problem common to both means for fluid mixture, i.e., from separate solution containers or from separate chambers in a single container, is the inability to know when a homogenous solution has been achieved upon mixing. A completely homogenous solution is desirable for optimum benefit to the patient and the avoidance of any possible harm resulting from incomplete mixture. Medical personnel solve this problem by vigorously mixing the two solutions for a period of time which is most assuredly longer than what is necessary to provide a complete homogenous solution. This is a waste of valuable time by a nurse or pharmacist, particularly where many solutions must be prepared.

With double chamber flexible plastic containers the total fluid volume in the container typically will not all be contained within a single chamber after mixing. This is especially true when the volumes of each of the two supply solutions are approximately equal, as in the case of amino acid and dextrose. The container could of course be made large enough such that a single chamber could hold the entire fluid volume, but this results in a very large container which is bulky, awkward and takes a great amount of additional material to manufacture.

Because of the need to ensure complete mixing and because the total solution volume is greater than the volume of a single chamber, medical personnel actively mix the two solutions, i.e., they squeeze one of the chamber contents into the other chamber. The procedure is then reversed by squeezing the other chamber. This is a source of additional time loss. In the case of a large hospital, the active mixing of the two chambers for a large number of containers takes considerable time.

The container embodying my invention allows for lengthy product storage time and allows for mixing of the supply solutions in a closed system. The container of my invention allows for passive mixing such that the container need not be squeezed by medical personnel. Most importantly, I have discovered means for providing a positive check that a homogenous solution has been achieved, thereby both preventing an improper mixture and eliminating unnecessary over-mixing. In addition, the container of my invention is compact and efficient in that after mixing both chambers may be almost full, while still allowing for the positive check to be made.

SUMMARY OF THE INVENTION

The present invention provides for the passive mixing of two supply solutions having different specific gravities into a single homogenous solution in a closed environment for the prevention of contamination during mixing. The container embodying the invention includes uniquely structured, selectively communicating chambers which provide for a positive check that a single homogenous solution has been achieved, eliminating the guess work in providing a proper homogenous solution. In the preferred embodiment, the container wall is of a flexible, plastic material. Container dividing means spans the interior defined by the container wall, dividing the container into upper and lower chambers. In the preferred embodiment the container dividing means is a formed heat seal between opposed sections of the flexible plastic container wall. The top of the lower chamber is disposed at an elevation higher than the bottom of the upper chamber. Two closure means such as breakaway valves are mounted through the container dividing means, one providing selective communication between the top portion of the lower chamber and the upper chamber and the other closure means providing selective communication between the bottom portion of the upper chamber and the lower chamber. At least that section of the container wall which defines the top and bottom portions is transparent.

Upon opening both closure means the chambers are placed in fluid flow communication and solution transfer may be effected between the upper and lower chambers by simply hanging the container, without pressing upon one of the chambers. When solution transfer stops, the container may be inverted and hung from its opposite end and the process repeated. The operator obtains a positive reading that a completely homogenous solution has been achieved. The positive check is provided by viewing the solution level or menicus in each chamber after solution transfer stops. If the solution levels are unequal, the container is inverted an additional time and the procedure repeated. If the solution levels are equal, the operator knows that the two supply solutions, which were of different specific gravities, are now thoroughly mixed. The homogenous solution is now ready for administration to the patient. The container preferably has an administration port such that the spike of a parenteral fluid administration set may be inserted therethrough for direct delivery of the homogenous solution to the patient.

The ability to obtain an accurate positive check of homogeneity is made possible by the configuration of the top portion of the lower chamber and the bottom portion of the upper chamber. Preferably, the top and bottom portions are narrow in width relative to the width of the container. The narrow top and bottom portions accentuate the difference between the menisci if a homogenous solution has not yet been achieved.

DETAILED DESCRIPTION OF THE PREFERRED EMBODIMENTS

Figure 1:
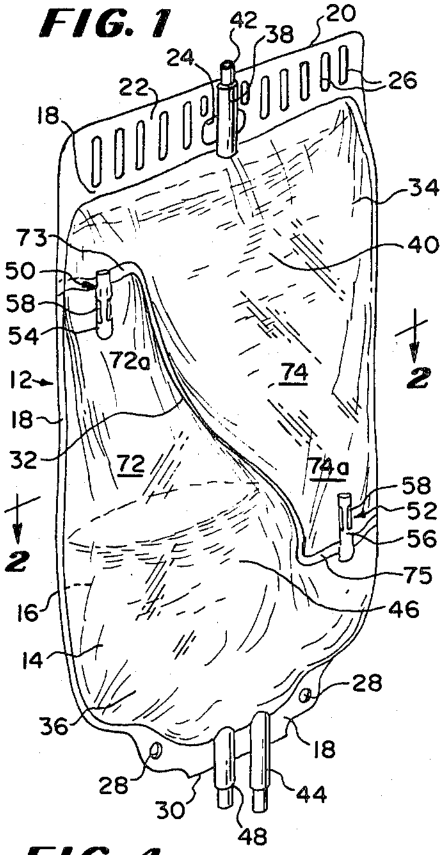
FIG. 1 is a perspective view of the container of my invention.
Figure 2:
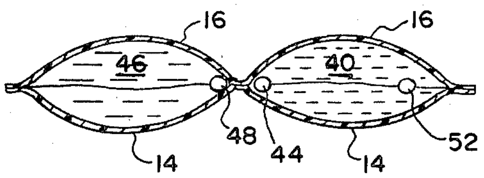
FIG. 2 is a cross-sectional view taken at line 2—2 in FIG. 1.

As seen in FIGS. 1-8 there is provided a container 12. The container wall is formed by flexible plastic sheets 14, 16 joined by means such as a heat seal 18 along the periphery of the plastic sheets 14, 16. A somewhat wider heat seal 18 is formed at the top end 20 of the container forming a flange 22. The flange provides for a stronger heat seal and may help the container to keep its shape upon hanging from top hanger opening 24. Ridges 26 are provided on the flange such that when the flange is folded over onto the container wall during packaging the flange does not stick to the container wall. Bottom hanger openings 28 are provided along that portion of the heat seal 18 at the bottom end 30 of the container.

Container dividing means is provided by a container dividing heat seal 32 between the flexible plastic sheets 14, 16 such that the container is divided into upper and lower chambers 34, 36. The flexible plastic sheets 14, 16 and the container dividing heat seal 32 define the boundaries of the upper and lower chambers 34, 36. A fill port 38 comprising a plastic tube is mounted through the heat seal 18 at the top 20 of the container 12, such that a supply solution 40 may be introduced into the upper chamber 34 during manufacture. The fill port 38 may include a smaller diameter tube 42 having a piercable membrane (not shown) therein, the smaller diameter tube 42 being bonded to the tube of the fill port 38 after introduction of the supply solution.

An administration port 44 of similar construction to the fill port 38 is provided at the bottom 30 of the container 12. Before the administration port is sealed it may be used to fill the lower chamber 36 with an other supply solution 46. The supply solutions 40, 46 have different specific gravities. Near the administration port 44 is an injection site 48 of conventional construction, such as the fill port 38 and administration port 44. A latex plug (not shown) may be mounted at the end of the injection site 48.

The container dividing means is constructed such that there is defined a top portion 72 of the lower chamber 36, disposed at the same elevation as a defined bottom portion 74 of the upper chamber 34. The top 73 of the lower chamber 36 is thus at an elevation higher than the bottom 75 of the upper chamber 34. Columnar-like, narrow segments **72*a*, 74*a* of the top and bottom portions 72, 74 respectively, are preferably included, disposed at the distal ends of the top and bottom portions 72, 74. As explained below, the top and bottom portions 72, 74, and especially the narrow segments 72*a*, 74*a*** thereof, provide for a positive visual test that a thorough mixture has been obtained, resulting in a single homogenous solution.

Figure 3:
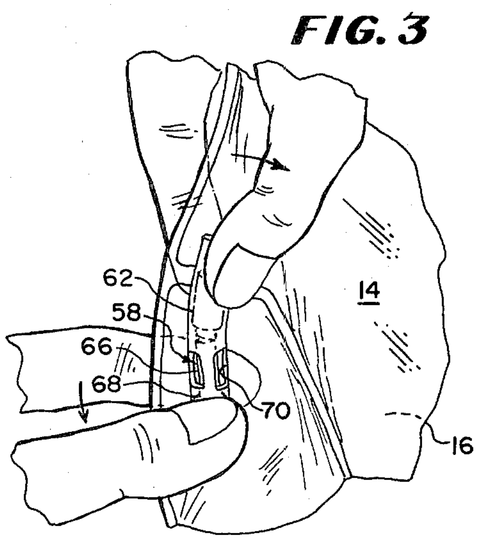
FIG. 3 is a fragmentary perspective view illustrating the procedure for opening the valves while maintaining a closed system.
Figure 11:
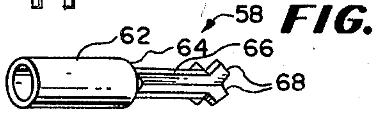
FIG. 11 is a perspective view of a breakaway valve used in the container.

Closure means 50, 52 are mounted through the container dividing means such that segregation of the upper and lower chambers 34, 36 is maintained until the closure means 50, 52 are selectively opened. In the preferred embodiment one closure means 50 is mounted between the top portion 72 of the lower chamber 36 and the upper chamber 34. The other closure means 52 is mounted between the bottom portion 74 of the upper chamber 34 and the lower chamber 36. Also, the closure means 50, 52 are preferably mounted substantially vertically, the upper chamber 34 thus being above the top portion 72 at closure means 50 and being above the lower chamber 36 at closure means 52. As described in above-referenced patent application Ser. No. 246,479, the closure means 50, 52 may each include retention means such as plastic tubes 54, 56. Breakaway valves 58 are mounted within the plastic tubes 54, 56. Plastic breakaway valves are known. In the preferred embodiment, the breakaway valve is as described in allowed U.S. patent application Ser. No. 086,102, filed Oct. 18, 1979, now U.S. Pat. No. 4,340,049 and assigned to the present assignee; however, other constructions of breakaway valves may be employed. Indeed, other types of closure means are also possible in the container of the present invention. As seen in the allowed application and in FIG. 11 of the present application, each breakaway valve 58 includes a hollow, tubular portion 62 having a closed end 64. A handle 66 extends from and is formed integrally with the closed end. A zone of weakness is provided at the juncture of the handle with the closed end such that at least a portion of the closed end 64 is removable by manipulating the handle 66 in a bending motion as shown in FIG. 3, to separate the closed end 64 from the tubular portion 62, thereby permitting fluid flow through the tubular portion and around the handle 66. The handle 66 of each valve 58 preferably includes projection means 68 extending radially outwardly from the handle to provide sufficient frictional contact with the interior surface of the plastic tubes 54, 56 such that the handle 66 can be moved away from the tubular portion 62 and remain in any selected position in the tubes 54, 56 away from the tubular portion, to assure uninterrupted fluid flow. Additionally, the frictional contact between the projection means 68 and the plastic tube prevents the handle from floating freely in either the upper or lower chamber. Slots 70 or other openings are provided in the plastic tubes 54, 56 to facilitate quicker fluid flow through the closure means upon opening of the breakaway valves 58.

To mix the two supply solutions, both closure means 50, 52 are opened such as shown in FIG. 3. The flexible plastic sheets 14, 16 are grasped such that the closure means can be manipulated externally of the container 12. Each breakaway valve 58 is broken by bending the valve, thereby breaking the valve 58 at the weakened zone. In one sample container built in accordance with the invention, breakaway valves were provided having a diameter of approximately ½ inch, thus providing for relatively quick fluid flow through the closure means 50, 52.

Figure 4:
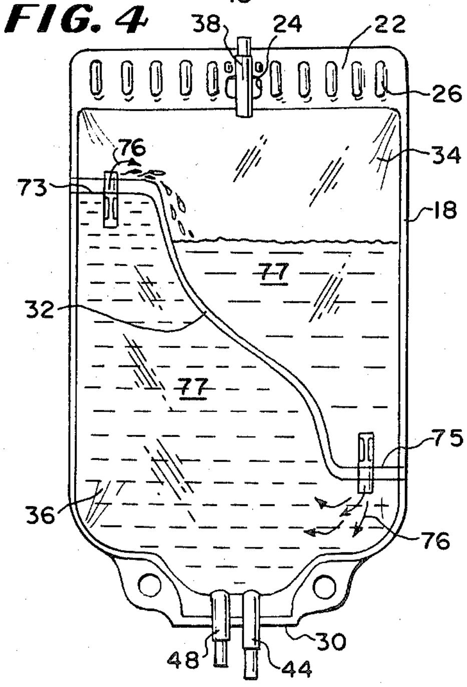
FIG. 4 is a front elevational view of the container during passive mixing, illustrating fluid flow through both valves.

After both closure means 50, 52 are opened the operator may simply hold the container at the flange 22 or suspend the container 12 from a hook (not shown) through the top hanger opening 24. The supply solution having a higher specific gravity, such as amino acid, may have been stored in the upper chamber 34. The supply solution having a lower specific gravity, such as dextrose, may be in the lower chamber 36. Upon breaking the closure means 50, 52 and suspending the container with the top end 20 up, the heavier supply solution flows from the upper chamber 34 into the lower chamber 36 through closure means 52 communicating between the narrow segment 74*a* of the upper chamber 34 and the lower chamber 36. The solution level in the upper chamber therefore drops and the solution level in the lower chamber 36 therefore rises. As seen in FIG. 4, the fluid levels in the unopened chambers may have been such that upon opening of the closure means 50, 52 the fluid level in the lower chamber rises so high that some of the fluid flows out of the lower chamber 36 through the closure means 50 communicating between the narrow segment 72*a* of the lower chamber 36 and the upper chamber 34. The fluid flow is shown generally by arrows 76. It must be stressed, however, that passive mixing and the positive check of homogenous solution attainment provided by the present invention is also possible when fluid flows through only one of the two closure means 50, 52 at a given time.

Figure 5:
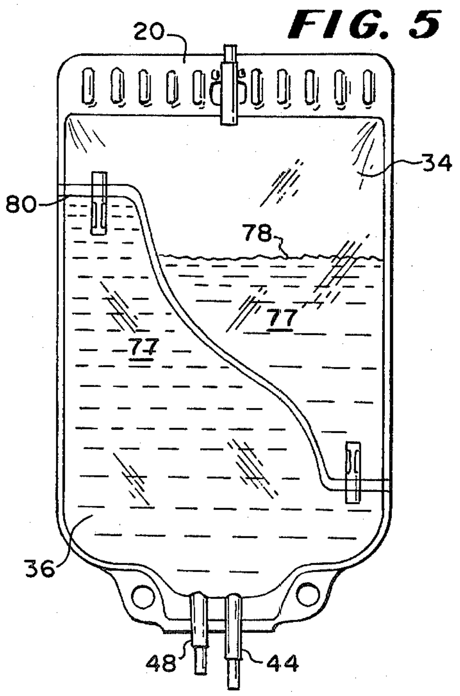
FIG. 5 is a front elevational view of the container in an equilibrium state after mixing but before a homogenous solution is achieved.
Figure 6:
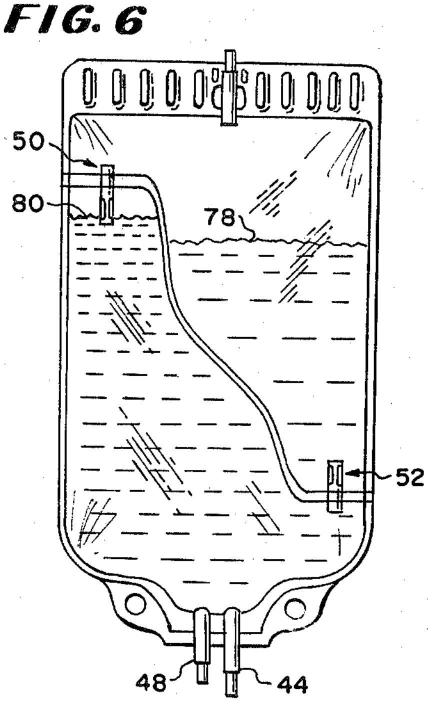
FIG. 6 is a front elevational view after mixing wherein fluid flow has occured through only one valve, before a homogenous solution has been achieved.

Eventually, fluid transfer between the two chambers stops and the fluid level in each chamber reaches an equilibrium state as shown in FIG. 5. Partially mixed solution 77 is now in each chamber 34, 36. In FIG. 5 the solutions have achieved an equilibrium state where the lower chamber 36 is entirely full. The lower chamber 36 need not be full in the equilibrium state. Factors such as the difference in specific gravity between the two supply solutions and the volume of fluid in each chamber before the valves 58 are opened will affect the solution levels in the chambers at the equilibrium state. For example, FIG. 6 shows another possible equilibrium state after solution transfer has been completed during suspension of the container 12 with the top end 20 up. In this case, it is assumed that no solution has gone through the closure means 50 from the top portion 72 into the upper chamber 34. As a further alternate equilibrium state, after this first solution transfer the solution level in the lower chamber 36 may indeed be lower than the solution level in the upper chamber 34.

Figure 7:
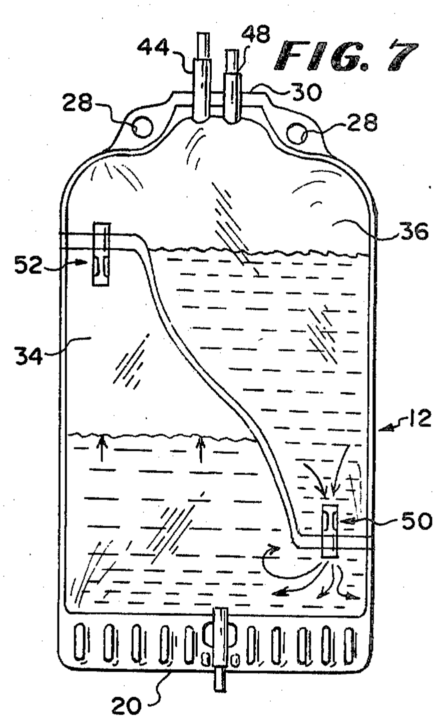
FIG. 7 is a front elevational view illustrating solution mixing with the bag in an inverted position.

Most likely the solutions will not have thoroughly mixed after being held in one positiion upon breaking of the closure means 50, 52. Incomplete mixing can be verified by noting that the upper chamber meniscus 78 is not at the same elevation as the lower chamber meniscus 80. The container 12 is then inverted as shown in FIG. 7 such that it may be held from the bottom end 30 of the container 12 at the administration port 44 and injection site 48. Alternatively, hangers (not shown) may be placed through the bottom hanger openings 28 to suspend the container 12 in the inverted position. The solution in the lower chamber 36 then flows through closure means 50 into the upper chamber 34 causing the solution level in each chamber to change.

In the case of amino acids and dextrose as the two supply solutions 40, 46, it has been found that two mixing steps are not sufficient to provide a homogenous solution. Therefore, the container 12 is inverted once again with the top end 20 up whereupon solution transfer again occurs.

Figure 8:
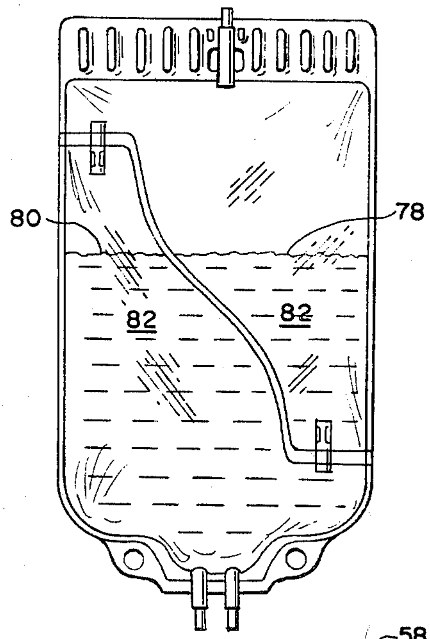
FIG. 8 illustrates the container after complete mixture such that a homogenous solution is achieved.

FIG. 8 illustrates the container after the third mixing iteration. A homogenous solution 82 now exists. The operator knows that a homogenous solution is present because the menisci 78, 80 in the upper and lower chambers 34, 36, respectively, are at a virtually identical elevation. Achievement of a homogenous solution 82 may take less or more than three mixing steps, depending upon the volume and specific gravities of the supply solutions 40, 46; the key feature is that the operator knows when a homogenous solution 82 has been achieved. The operator need not worry about whether the solutions have been properly mixed. The operator need not compensate for this uncertainty by overmixing, which takes additional time, to provide the proper mixture. Further, the container of the present invention allows for passive mixing, i.e., after opening the closures means 50, 52 the container 12 may be simply held or suspended to allow solution transfer. After solution transfer stops the menisci are checked; if the solution levels are unequal, the container is inverted and the process repeated until they are indeed equal.

It is preferred that the narrow segments 72*a*, 74*a* are substantially thinner in width than the remainder of the chambers 34, 36, thus magnifying the difference in fluid level between the two chambers until a homogenous solution is obtained. The container 12 is designed such that the volume of each individual chamber 34, 36 is less than the total solution volume stored in the container 12, thereby allowing for the positive check for the homogenous solution. The individual chamber volumes can be designed based upon the specific gravities and volumes of the two supply solutions 40, 46 to be stored therein, such that upon breaking the closure means 50, 52 and effecting solution transfer the solution levels in each equilibrium state reached after each mixing iteration are within at least one of the narrow segments 72*a*, 74*a* of the top and bottom portions 72, 74.

Figure 9:
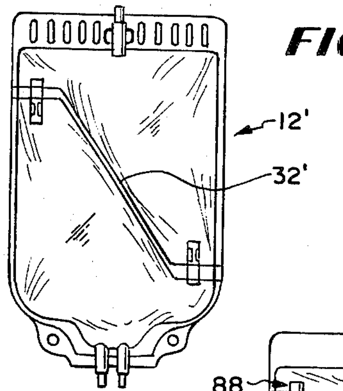
FIG. 9 is an alternate embodiment of my invention, having a different chamber configuration.

In FIG. 9 there is illustrated an alternative container 12' which embodies the present invention, having container dividing means of a different configuration. Here, the container dividing heat seal 32' is angular. Passive mixing is still facilitated and a positive check for homogenous solution achievement is still provided. The top and bottom portions do not include columnar-like segments however, so that the discrepancy between the solution levels in the two chambers is not as great during the mixing steps as with the container 12.

Figure 10:
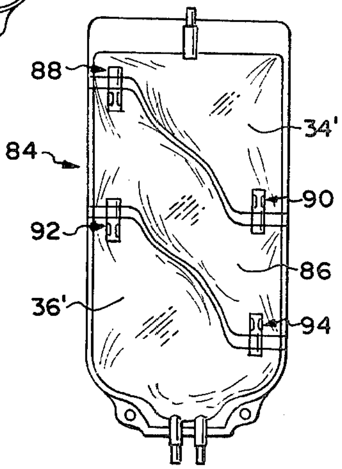
FIG. 10 is a further alternate embodiment of my invention illustrating a container having three selectively communicating chambers.

In FIG. 10 there is shown a second modification of the invention. A container 84 includes upper chamber 34', lower chamber 36' and middle chamber 86. In such a container configuration three different supply solutions may be stored. Depending on the desired order for forming the homogenous solution, the contents of upper and middle chambers 34', 86 may be mixed first by opening closure means 88, 90 and then mixing the resulting mixture with the contents of the lower chamber 36' by opening closure means 92, 94. Alternatively, all closure means 88, 90, 92, 94 may be opened at the same time before proceeding with the passive mixing steps.

While several embodiments of the present invention have been described in detail herein and shown in the accompanying drawings, it will be evident that various further modifications are possible without departing from the scope of the invention.

What is claimed is:

1. A container for passively mixing two supply solutions having different specific gravities into a single homogenous solution and for providing a positive check that a single homogenous solution has been achieved, the container comprising:

a container wall;

container dividing means spanning the interior defined by said container wall, said container dividing means and container wall defining an upper chamber and a lower chamber, one of the supply solutions carried in said upper chamber and the other of the supply solutions carried in said lower chamber;

a top portion of said lower chamber disposed at the same elevation as a bottom portion of said upper chamber so that the top of said lower chamber is at an elevation higher than the bottom of said upper chamber;

at least a section of said container wall being transparent to enable viewing of the interior defined by said top and bottom portions;

two closure means mounted through said container dividing means for selective communication between said upper and lower chambers, one of said closure means mounted through said dividing means between said top portion of said lower chamber and said upper chamber, the other of said closure means mounted through said dividing means between said bottom portion of said upper chamber and said lower chamber;

such that upon opening said closure means, solution transfer is effected between said upper and lower chambers through at least one of said closure means until the solution level in each of said chambers is equal, the equal solution levels providing a positive indication that the two supply solutions have been mixed into a single homogenous solution within said container.

2. A container as in claim 1, wherein said container wall is flexible plastic and wherein said container dividing means is a formed heat seal between opposed sections of said flexible plastic container wall.

3. A container as in claim 1, further comprising an administration port assembly in said lower chamber which may be opened for permitting solution flow out of said container through said administration port assembly.

4. A container for storing separately two supply solutions having different specific gravities and for passiviely mixing the supply solutions into a single homogenous solution that is unstable over extended time periods, said container providing a positive check that a single homogenous solution has been achieved and comprising:

a container wall;

container dividing means spanning the interior defined by said container wall, said container dividing means and container wall defining an upper chamber and a lower chamber, one of the supply solutions carried in said upper chamber and the other of the supply solutions carried in said lower chamber;

a top portion of said lower chamber disposed at the same elevation as a bottom portion of said upper chamber so that the top of said lower chamber is at an elevation higher than the bottom of said upper chamber;

at least a section of said container wall being transparent to enable viewing of the interior defined by said top and bottom portions;

two closure means mounted through said container dividing means for selective communication between said upper and lower chambers, one of said closure means mounted substantially vertically through said dividing means between said top portion of said lower chamber and said upper chamber, the other of said closure means mounted substantially vertically through said dividing means between said bottom portion of said upper chamber and said lower chamber;

such that upon opening said closure means, solution transfer may be effected between said upper and lower chambers through at least one of said closure means until the solution level in each of said chambers is equal, the equal solution levels providing a positive indication that the two supply solutions have been mixed into a single homogenous solution within said container.

5. A container for storing separately two supply solutions having different specific gravities and for passively mixing the supply solutions into a single homogenous medical solution that is unstable over extended time periods, said container providing a positive check that a single homogenous medical solution has been achieved and comprising:

a container wall including flexible plastic sheets;

container dividing means spanning the interior defined by said container wall, said container dividing means and container wall defining an upper chamber and a lower chamber, one of the supply solutions carried in said upper chamber and the other of the supply solutions carried in said lower chamber;

a top portion of said lower chamber disposed at the same elevation as a bottom portion of said upper chamber so that the top of said lower chamber is at an elevation higher than the bottom of said upper chamber;

at least a section of said container wall being transparent to enable viewing of the interior defined by said top and bottom portions;

two closure means mounted through said container dividing means for selective communication between said upper and lower chambers, one of said closure means mounted substantially vertically through said dividing means between said top portion of said lower chamber and said upper chamber, the other of said closure means mounted substantially vertically through said dividing means between said bottom portion of said upper chamber and said lower chamber, said closure means being opened by container-external manipulation of said container wall and closure means;

such that upon opening said closure means, solution transfer may be effected between said upper and lower chambers through at least one of said closure means until the solution level in each of said chambers is equal, the equal solution levels providing a positive indication that the two supply solutions have been mixed into a single homogenous solution within said container.

6. A container as in claims 1, 4 or 5, wherein the volume of each of the upper and lower chambers is less than the total solution volume carried by said container.

7. The container as in claims 1, 4 or 5, further comprising a columnar-like segment in at least one of said top and bottom portions, said segment being narrow relative to the width of its respective chamber.

8. A method for passively mixing two supply solutions having different specific gravities into a single homogenous solution in a closed environment and for providing a positive check that a single homogenous solution has been achieved, the container including a container wall, container dividing means spanning the interior defined by said container wall, the container dividing means and container wall defining an upper chamber and a lower chamber, whereby one of the supply solutions is carried in the upper chamber and the other of the supply solutions is carried in the lower chamber, the container further including a top portion of the lower chamber which is disposed at the same elevation as the bottom portion of the upper chamber, at least a section of the container wall being transparent to enable viewing of the interior defined by the top and bottom portions, two closure means mounted through the container dividing means for selective communication between the upper and lower chambers, one of the closure means being mounted through the dividing means between the top portion of the lower chamber and the upper chamber, the other of the closure means mounted through the dividing means between the bottom portion of the upper chamber and the lower chamber, the method comprising:

manually opening both of the closure means;

suspending the container such that solution transfer is effected between the upper and lower chambers until an equilibrium state is reached;

visually inspecting the meniscus in each of the upper and lower chambers such that if the menisci are at equal elevations a homogenous solution has been achieved;

inverting the container and repeating the steps of suspension for solution transfer and visual inspection until the menisci in the upper and lower chambers are at substantially the same level.

* * * * *